United States Patent [19]
Anderson et al.

[11] Patent Number: 5,442,049
[45] Date of Patent: Aug. 15, 1995

[54] OLIGONUCLEOTIDES FOR MODULATING THE EFFECTS OF CYTOMEGALOVIRUS INFECTIONS

[75] Inventors: Kevin Anderson, Carlsbad, Calif.; Kenneth Draper, Boulder, Colo.; Brenda Baker, Encinitas, Calif.

[73] Assignee: Isis Pharmaceuticals, Inc., Carlsbad, Calif.

[21] Appl. No.: 9,263

[22] Filed: Jan. 25, 1993

Related U.S. Application Data

[63] Continuation-in-part of Ser. No. 927,506, filed as PCT/US 91/05815, Aug. 14, 1991.

[51] Int. Cl.$^6$ .................... C07H 21/04; A61K 48/00
[52] U.S. Cl. .................................................. 536/24.5
[58] Field of Search ........................ 536/24.5; 514/44

[56] References Cited

U.S. PATENT DOCUMENTS 5,034,506  7/1991  Summerton et al. ............... 528/391

OTHER PUBLICATIONS

Kouzarides et al., J. Virol. 61 V.):125–133 (Jan. 1987).
Ratner, Bio/Technology 7:207 (Mar. 1989).
Stenberg et al., J. Virol. 49 V.):190–199 (Jan. 1984). ibid. 56(3):665–675 (Dec. 1985).
Stein et al., Science 261:1004–1112 (20 Aug. 1993).
Cohen, Jack S., Oligodeoxynucleotides: Antisense Inhibitors of Gene Expression, CRC Press: Boca Raton, Fla., 1989.
P. S. Miller & P.O.P. Ts'O, "A new approach to chemotherapy based on molecular biology and nucleic acid chemistry: Matagen (masking tape for gene expression)," Anti–Cancer Drug Design 1987, 2:117–128.
Nielsen, Peter E., et al., "Sequence—Selective Recognition of DNA by Strand Displacement with a Tyymine—Substituted Polyamide," Science, 254:1497–1500, 1991.
Rothenberg et al., "Oligodeoxynucleotides as Anti-–Sense Inhibitors of Gene Expression: Therapeutic Implicaitons," J. Natl. Cancer Inst., 81:1539–1544, 1989.
Zon, G. "Oligonucleotides Analogues as Potential Chemotherapeutic Agents," Pharmaceutical Res., 5:539–549, 1988.

Primary Examiner—Stephanie W. Zitomer
Attorney, Agent, or Firm—Jane Massey Licata

[57] ABSTRACT

Compositions and methods for modulating the effects of cytomegalovirus (CMV) infections are disclosed, comprising contacting CMV mRNA with an oligonucleotide which can bind with at least portions of the CMV RNA. In accordance with the preferred embodiments, oligonucleotides such as ISIS 2922 are designed to bind with portions of the CMV mRNAs which code for the IE1, IE2 or DNA polymerase proteins. In accordance with a preferred embodiment, methods of treatment of human cytomegalovirus are disclosed.

1 Claim, 6 Drawing Sheets

SEQUENCE LISTING ( 1 ) GENERAL INFORMATION:

( i i i ) NUMBER OF SEQUENCES: 88

( 2 ) INFORMATION FOR SEQ ID NO:1:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:1:

GTGTCAAGTG GCACCATACG           20

( 2 ) INFORMATION FOR SEQ ID NO:2:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

TGGAAAGTGT ACACAGGCGA A           21

( 2 ) INFORMATION FOR SEQ ID NO:3:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: DNA (genomic)

( i i i ) HYPOTHETICAL: NO (i v) ANTI-SENSE: YES (x i) SEQUENCE DESCRIPTION: SEQ ID NO:3:

GGGTTGAAAA ACATAGCGGA C  21

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:4:

GAGGACTCCA TCGTGTCAAG  20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:5:

GTGGGCCATG ATGATGGAAG G  21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:6:

GTCCCGTAGA TGACCCGCGC C  21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:7:

CGGCGCAGAT TGCAAGGGCG G  21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

GCCGGAGCCG GGTGAAACGC C        21

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:9:

CGCCGTCCGG ACACCGGGCG C        21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:10:

ACCGGGAAAC CACGCCGGCG G        21

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:11:

CCGCGCCCTC TTCTTTGCCG G        21

( 2 ) INFORMATION FOR SEQ ID NO:12:

( i ) SEQUENCE CHARACTERISTICS:
        ( A ) LENGTH: 21 base pairs
        ( B ) TYPE: nucleic acid ( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:12:

GGTACTTACG TCACTCTTGG C                    21

( 2 ) INFORMATION FOR SEQ ID NO:13:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:13:

GACGGTGACT GCAGAAAAGA C                    21

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:14:

GACACGTACC GTGGCACCTT G                    21

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:15:

GTCTCGGGCC TAAACACATG                      20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:16:

CAGACTTACC GACTTCTGCC     20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:17:

CTGTTTGACT GTAGAGGAGG     20

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:18:

GGGTCCTTCA TCTGGGAGAG C     21

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:19:

CGGCTCACCT CGTCAATCTT G     21

( 2 ) INFORMATION FOR SEQ ID NO:20:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:20:

GCGCACCATG ACCTGTTTGG G     21

( 2 ) INFORMATION FOR SEQ ID NO:21:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:21:

GTTTTGCGCG GTTTCTTACG C             21

( 2 ) INFORMATION FOR SEQ ID NO:22:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:22:

GCGTTTGCTC TTCTTCTTGC G             21

( 2 ) INFORMATION FOR SEQ ID NO:23:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:23:

CGTCTCCAGG CGATCTGACG C             21

( 2 ) INFORMATION FOR SEQ ID NO:24:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:24:

TGGCGTCTCC AGGCGATCTG A             21

( 2 ) INFORMATION FOR SEQ ID NO:25:

( i ) SEQUENCE CHARACTERISTICS:
    ( A ) LENGTH: 20 base pairs ( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:25:

TCTGAGTAGC AGAGGAGCTC 20

( 2 ) INFORMATION FOR SEQ ID NO:26:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:26:

CTCCACGCGA ATTTTAACAC A 21

( 2 ) INFORMATION FOR SEQ ID NO:27:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:27:

ACTCGGGCTG CCACTTGACA G 21

( 2 ) INFORMATION FOR SEQ ID NO:28:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:28:

CGTTTGCTCT TCTTCTTGC 19

( 2 ) INFORMATION FOR SEQ ID NO:29:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

(iii) HYPOTHETICAL: NO (iv) ANTI-SENSE: YES (xi) SEQUENCE DESCRIPTION: SEQ ID NO:29:

GTTTGCTCTT CTTCTTG                                                                                      17

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:30:

GCGTTTGCTC TTCTTCTTGC                                                                                   20

(2) INFORMATION FOR SEQ ID NO:31:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:31:

GCGTTTGCTC TTCTTCTTG                                                                                    19

(2) INFORMATION FOR SEQ ID NO:32:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:32:

GCGTTTGCTC TTCTTCTT                                                                                     18

(2) INFORMATION FOR SEQ ID NO:33:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:33:

GCGTTTGCTC TTCTTCT 17

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:34:

CGTTTGCTCT TCTTCTTGCG 20

(2) INFORMATION FOR SEQ ID NO:35:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:35:

GTTTGCTCTT CTTCTTGCG 19

(2) INFORMATION FOR SEQ ID NO:36:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:36:

TTTGCTCTTC TTCTTGCG 18

(2) INFORMATION FOR SEQ ID NO:37:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:37:

TTGCTCTTCT TCTTGCG 17

(2) INFORMATION FOR SEQ ID NO:38:

(i) SEQUENCE CHARACTERISTICS:

( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:38:

GCGTTTGCTC CTCTTCTTGC G 21

( 2 ) INFORMATION FOR SEQ ID NO:39:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:39:

GCGTTTTCTC TTCTGCTTGC G 21

( 2 ) INFORMATION FOR SEQ ID NO:40:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:40:

TCGGTTTCTC GTCTGCTTTC G 21

( 2 ) INFORMATION FOR SEQ ID NO:41:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:41:

GCGGTTTCTC TTCTGCTTTC G 21

( 2 ) INFORMATION FOR SEQ ID NO:42:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:42:

AGATGCGTTT GCTCTTCTTC T 21

( 2 ) INFORMATION FOR SEQ ID NO:43:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:43:

TTGCTCTTCT TCTTGCGGGG T 21

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:44:

TATGGAGGTC AAAACAGCGT G 21

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:45:

TGGATCGGTC CCGGTGTCTT C 21

( 2 ) INFORMATION FOR SEQ ID NO:46:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:46:

```
        ACCGTTCCCG GCCGCGGAGG C                                              21
```

( 2 ) INFORMATION FOR SEQ ID NO:47:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:47:

```
        GGGGAATCCG CGTTCCAATG C                                              21
```

( 2 ) INFORMATION FOR SEQ ID NO:48:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:48:

```
        CACCCGCGAC CGCACCGCCG G                                              21
```

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:49:

```
        CAGATACGGG TTGAAAAACA T                                              21
```

( 2 ) INFORMATION FOR SEQ ID NO:50:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:50:

```
        TGGTGTAAGG CGGAGCCGCC G                                              21
```

( 2 ) INFORMATION FOR SEQ ID NO:51:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:51:

TGGTGTAAGG CGGGGCCGCC G    21

( 2 ) INFORMATION FOR SEQ ID NO:52:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:52:

CAGACGGGCC AGGGCCAGAA G    21

( 2 ) INFORMATION FOR SEQ ID NO:53:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:53:

CAGACGGGCC GGGGCCAGAA G    21

( 2 ) INFORMATION FOR SEQ ID NO:54:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:54:

TCCTGCGTGC CAGTCTGTCC G    21

( 2 ) INFORMATION FOR SEQ ID NO:55:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:55:

GTAGCCGTTT TTGCGATGTC G   21

(2) INFORMATION FOR SEQ ID NO:56:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:56:

CCTCCTGGTT CAGACGTTCT C   21

(2) INFORMATION FOR SEQ ID NO:57:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:57:

CAGTTTAACC CCGTATATCA C   21

(2) INFORMATION FOR SEQ ID NO:58:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: YES (x i) SEQUENCE DESCRIPTION: SEQ ID NO:58:

CAGCTTACGA AGCAAAATCA C   21

(2) INFORMATION FOR SEQ ID NO:59:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(i i i) HYPOTHETICAL: NO (i v) ANTI-SENSE: YES ( x i ) SEQUENCE DESCRIPTION: SEQ ID NO:59:

CATAGCGGAC CGTGAGAGGC T           21

( 2 ) INFORMATION FOR SEQ ID NO:60:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:60:

CATAGCGGAC CGTGGGAGGC T           21

( 2 ) INFORMATION FOR SEQ ID NO:61:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:61:

CATAGCGGAC CGTGAGGGGC T           21

( 2 ) INFORMATION FOR SEQ ID NO:62:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:62:

CATAGCGGAC CGTGGGGGGC T           21

( 2 ) INFORMATION FOR SEQ ID NO:63:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:63:

AAACCCACGG CGGGGCTGTG T           21

( 2 ) INFORMATION FOR SEQ ID NO:64:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:64:

CGCGCGATGG CCCCGGCCTG C                                      21

( 2 ) INFORMATION FOR SEQ ID NO:65:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:65:

GGACCGGGAC CACCGTCGTC                                        20

( 2 ) INFORMATION FOR SEQ ID NO:66:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:66:

GTCCGCTATG TTTTTCAACC C                                      21

( 2 ) INFORMATION FOR SEQ ID NO:67:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:67:

CCTTCCATCA TCATGGCCCA C                                      21

( 2 ) INFORMATION FOR SEQ ID NO:68:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:68:

GGCGCGGGTC ATCTACGGGA C     21

( 2 ) INFORMATION FOR SEQ ID NO:69:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:69:

CCGCTGTGCC CGGCGACGCG G     21

( 2 ) INFORMATION FOR SEQ ID NO:70:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:70:

CCGCCCTTGC AATCTGCGCC G     21

( 2 ) INFORMATION FOR SEQ ID NO:71:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:71:

GGCGTTTCAC CCGGCTCCGG C     21

( 2 ) INFORMATION FOR SEQ ID NO:72:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:72:

GCGCCCGGTG TCCGGACGGC G        21

( 2 ) INFORMATION FOR SEQ ID NO:73:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:73:

CCGCCGGCGT GGTTTCCCGG T        21

( 2 ) INFORMATION FOR SEQ ID NO:74:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:74:

CCGGCAAAGA AGAGGGCGCG G        21

( 2 ) INFORMATION FOR SEQ ID NO:75:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:75:

GTGAACCGTC AGATCGCCTG G        21

( 2 ) INFORMATION FOR SEQ ID NO:76:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:76:

CTTGACACGA TGGAGTCCTC        20

( 2 ) INFORMATION FOR SEQ ID NO:77:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:77:

GCCAAGAGTG ACGTAAGTAC C          21

( 2 ) INFORMATION FOR SEQ ID NO:78:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:78:

GTCTTTTCTG CAGTCACCGT C          21

( 2 ) INFORMATION FOR SEQ ID NO:79:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:79:

CAAGGTGCCA CGGTACGTGT C          21

( 2 ) INFORMATION FOR SEQ ID NO:80:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:80:

CATGTGTTTA GGCCCGAGAC          20

( 2 ) INFORMATION FOR SEQ ID NO:81:

( i ) SEQUENCE CHARACTERISTICS:
        ( A ) LENGTH: 20 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:81:

GGCAGAACTC GGTAAGTCTG    20

(2) INFORMATION FOR SEQ ID NO:82:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:82:

CCTCCTCTAC AGTCAAACAG    20

(2) INFORMATION FOR SEQ ID NO:83:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:83:

GCGCCTATCA TGCTGCCCCT C    21

(2) INFORMATION FOR SEQ ID NO:84:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:84:

GCTCTCCCAG ATGAACCACC C    21

(2) INFORMATION FOR SEQ ID NO:85:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (i v) ANTI-SENSE: NO (x i) SEQUENCE DESCRIPTION: SEQ ID NO:85:

CAAGATTGAC GAGGTGAGCC G                                      21

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:86:

CCCAAACAGG TCATGGTGCG C                                      21

(2) INFORMATION FOR SEQ ID NO:87:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:87:

GCGTAAGAAA CCGCGCAAAA C                                      21

(2) INFORMATION FOR SEQ ID NO:88:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:88:

CGCAAGAAGA AGAGCAAACG C                                      21

OLIGONUCLEOTIDES FOR MODULATING THE EFFECTS OF CYTOMEGALOVIRUS INFECTIONS

INTRODUCTION

This application is a continuation-in-part of Ser. No. 927,506, filed Nov. 19, 1992, which was filed as PCT international application PCT/US91/05815 on Aug. 14, 1991.

FIELD OF THE INVENTION

This invention relates to the design and synthesis of antisense oligonucleotides which can be administered to inhibit the replication of cytomegalovirus and treat cytomegalovirus infections. These compounds can be used either prophylactically or therapeutically to reduce the severity of disease caused by cytomegaloviruses. Oligonucleotides which are specifically hybridizable with selected DNA or RNA targets are described.

BACKGROUND OF THE INVENTION

Cytomegaloviruses (CMV's) are ubiquitous in nature and are the most common causes of intrauterine infection. Congenital infection is common in newborns of infected mothers. In some populations, as much as 10% of children display perinatal infections. In a small percentage of newborns, the infection is virulent, involving multiple organs. Pronounced involvement of the reticuloendothelial and central nervous system is typical; and the infection is a major cause of mental retardation. Careful testing demonstrates that as many as 50% of severely, prenatally infected adults may display neuropsychiatric disease or deafness. Although extraneural organs are usually spared chronic morbidity, the virus can be detected in the kidney for years.

In the adult, cytomegalovirus-induced mononucleosis is a lingering illness that causes significant morbidity. If it occurs in immunosuppressed patients, the disease is more severe, and it may be complicated by other infectious pathogens which may be fatal. Cytomegalovirus retinitis is a severe problem in immunosuppressed patients that often leads to blindness. Immunosuppressed patients are also very susceptible to CMV pneumonitis, which is one of the most lethal of human viral diseases. Although cytomegalovirus may play a role in the progression of HIV infection to AIDS by stimulating the transcription of the HIV long terminal repeats (LTR) in nontransformed co-infected T cells, histologic examination of adrenals and brains from AIDS patients has suggested that the adrenalitis, encephalitis and peripheral neuropathy were caused by CMV infection.

CMV is considered to be an oncogenic virus. In vitro, CMV can transform cells and stimulate growth. Both human and non-human cells can undergo transformation when incubated with CMV. Transformed cells contain CMV antigens that are oncogenic when inoculated into appropriate animals. Moreover, oncogenic potential has been associated with specific segments of the CMV genome.

Human CMV is a large, enveloped herpesvirus whose genome consists of a double-stranded DNA molecule which is approximately 240,000 nucleotides in length. This genome is the most complex of all DNA viruses and is approximately 50% larger than the genome of herpes simplex virus (HSV). Intact viral DNA is composed of contiguous long (L) and short (S) segments, each of which contains regions of unique DNA sequence flanked by homologous regions of repetitive sequence. As a group, the human CMV isolates share at least 80% sequence homology, making it nearly impossible to classify cytomegaloviruses into subgroups or subtypes, although variations in the restriction endonuclease patterns of various CMV DNA preparations are identifiable in epidemiologically unrelated strains. The DNA of the prototypic strain of CMV (AD 169) has been sequenced and reported to contain a conservative estimate of 175 unique translational open reading frames (ORFs). A number of the predicted CMV gene products show homology to other human herpesvirus gene products. At least 42 ORFs encode putative glycoproteins and several of the CMVORFs putatively encode proteins with amino acid homology to human opsin receptor proteins.

In permissive human fibroblasts, CMV gene expression is regulated by a cascade of genetic events that act at both the transcriptional and translational levels. CMV gene expression can be divided into three phases which resemble those of HSV defined as the immediate early (IE), early and late periods. Following adsorption, penetration and uncoating of the virus, a group of viral transcripts, immediate early messenger RNAs (IE mRNAs) are synthesized within 1–4 hours even in the presence of translational inhibitors such as cycloheximide. In the normal course of infection, the IE mRNAs are translated and their protein products are instrumental in the onset of early transcriptional events. At least 4 proteins are synthesized from IE mRNAs; of these, one is a glycoprotein. The IE1 and IE2 proteins are transcriptional activating factors for other CMV genes and the IE3 protein encompasses a region of the CMV genome which can transform NIH 3T3 cells in vitro. Early proteins are encoded by the mRNAs which are synthesized prior to viral DNA synthesis. A number of the early proteins play a role in nucleotide metabolism and DNA synthesis in the infected cell. After the onset of viral DNA synthesis, the transcription of the late mRNAs is maximal and probably reflects a template abundancy requirement similar to that observed for analogous HSV mRNAs. The late CMV proteins include the glycoprotein constituents of the viral envelope, the viral capsid proteins and other proteins which are necessary for assembly or structural integrity of the mature CMV particle and/or egress of the assembled virion from the infected cell. In addition to the transcriptional controls operant upon CMV gene expression, examples of post-transcriptional controls are known to influence the appearance of some CMV proteins. Splicing of mRNAs is more common than observed in HSV gene expression and the nucleotide sequence composition of the 5' nontranslated region in the cognate mRNA is reported to influence the synthesis of at least one early CMV protein.

Effective therapy for CMV has not yet been developed despite studies on a number of antivirals. Interferon, transfer factor, adenine arabinoside (Ara-A), acycloguanosine (Acyclovir, ACV) and certain combinations of these drugs have been ineffective in controlling CMV infection. Based on preclinical and clinical data, foscarnet (PFA) and ganciclovir (DHPG) show limited potential as antiviral agents. PFA treatment has resulted in the resolution of CMV retinitis in five AIDS patients. DHPG studies have shown efficacy against CMV retinitis or colitis. DHPG seems to be well tolerated by treated individuals, but the appearance of a reversible neutropenia, the emergence of resistant strains of CMV upon long-term administration, and the lack of efficacy against CMV pneumonitis limit the long term applications of this compound. The development of more effective and less-toxic therapeutic compounds and methods is needed for both acute and chronic use.

Classical therapeutics has generally focused upon interactions with proteins in efforts to moderate their disease causing or disease potentiating functions. Such therapeutic approaches have failed for cytomegalovirus infections. The present invention is directed to an alternative approach to the treatment of such infections, the antisense inhibition of cytomegalovirus gene expression through the mediation of oligonucleotides.

Antisense methodology is the complementary hybridization of relatively short oligonucleotides to single-stranded mRNA or single-stranded DNA, or even double stranded DNA, such that the normal, essential functions of these intracellular nucleic acids are disrupted. Hybridization is the sequence specific hydrogen bonding of oligonucleotides to Watson-Crick base pairs of RNA or single stranded DNA. Such base pairs are said to be complementary to one another.

The events which disrupt nucleic acid function are discussed by Cohen in *Oligonucleotides:Antisense Inhibitors of Gene Expression*, CRC Press, Boca Raton Fla., 1989, who proposes two possible types of terminating events. The first, hybridization arrest, denotes a terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides; P. S. Miller & P.O.P. Ts'O, *Anti-Cancer Drug Design* 1987, Vol. 2, pp. 117–128; and α-anomer oligonucleotides, Cohen J. S. ed., *Oligonucleotides: Antisense Inhibitors of Gene Expression*, CRC Press, Boca Raton Fla., 1989, are two of the most extensively studied antisense agents which are thought to disrupt nucleic acid function by hybridization arrest.

A second type of terminating event for antisense oligonucleotides involves enzymatic cleavage of the targeted RNA by intracellularRNase H. The oligonucleotide, which must be of the deoxyribo type, hybridizes with the targeted RNA and this duplex activates the RNase H enzyme to cleave the RNA strand, thus destroying the normal function of the RNA. Phosphorothioate oligonucleotides are a prominent example of an antisense agent which operates by this type of terminating event.

Considerable research is being directed to the application of oligonucleotides as antisense agents for therapeutic purposes. Applications of oligonucleotides as diagnostics, research reagents, and potential therapeutic agents require that the oligonucleotides be synthesized in large quantities, be transported across cell membranes or taken up by cells, appropriately hybridize to targeted RNA or DNA, and subsequently terminate or disrupt nucleic acid function. These critical functions depend on the initial stability of oligonucleotides towards nuclease degradation.

Oligonucleotides modified to exhibit resistance to nucleases, to activate the RNase H terminating event, and to hybridize with appropriate strength and fidelity to targeted RNA (or DNA) are greatly desired for antisense oligonucleotide diagnostics, therapeutics and research with cytomegaloviruses.

OBJECTS OF THE INVENTION

It is an object of this invention to provide oligonucleotides which are capable of hybridizing with at least a portion of RNA or DNA deriving from the IE1, IE2 or DNA polymerase genes of a cytomegalovirus to inhibit the flow of genetic information from DNA to protein.

It is a further object to provide oligonucleotides which can modulate the expression of cytomegalovirus through antisense interaction with selected DNA or RNA of the virus.

Yet another object of this invention is to provide methods of diagnostics and therapeutics for cytomegalovirus in animals.

Methods, materials and kits for detecting the presence or absence of cytomegalovirus in a sample suspected of containing it are further objects of the invention.

Novel oligonucleotides are other objects of the invention.

These and other objects will become apparent to persons of ordinary skill in the art from a review of the instant specification and appended claims.

SUMMARY OF THE INVENTION

In accordance with the present invention, methods of modulating the effects of cytomegalovirus infection are provided. Oligonucleotides having a sequence of nucleotide bases specifically hybridizable with a selected sequence of a cytomegalovirus DNA or RNA are provided. It has been determined that targeting cytomegalovirus DNA or RNA coding for the IE1, IE2, or DNA polymerase proteins is a key to the effective antisense therapy with these oligonucleotides. Methods for treating disease states by administering oligonucleotides, either alone or in combination with a pharmaceutically acceptable carrier, to animals suspected of having cytomegalovirus infections are provided.

This relationship is commonly denoted as "antisense." The oligonucleotides are able to inhibit the function of RNA—either its translation into protein, its translocation into the cytoplasm, or any other activity necessary to its overall biological function. The failure of the RNA to perform all or part of its function results in failure of a portion of the genome controlling the normal life cycle of the virus.

It has now been found that oligonucleotides can be designed especially for cytomegalovirus infections which are effective in diminishing the infection. It is preferred that oligonucleotides have between about 5 and about 50 nucleic acid base units. It is preferred that the oligonucleotide be specifically hybridizable with at least a portion of DNA or RNA coding for the CMV IE1, IE2, or DNA polymerase proteins. The oligonucleotide may be modified to reduce nuclease resistance and to increase their efficacy.

In accordance with preferred embodiments, the mRNA is interfered with to an extent sufficient to inhibit CMV replication. Thus, oligonucleotides which are capable of interacting with portions of CMV mRNA are comprehended. Animals suspected of having the disease are contacted with an oligonucleotide made in accordance with this invention. In particular, the present invention is believed to be effective in the treatment of cytomegalovirus infections, either prophylactically or therapeutically.

DETAILED DESCRIPTION OF PREFERRED EMBODIMENTS

Figure 1:
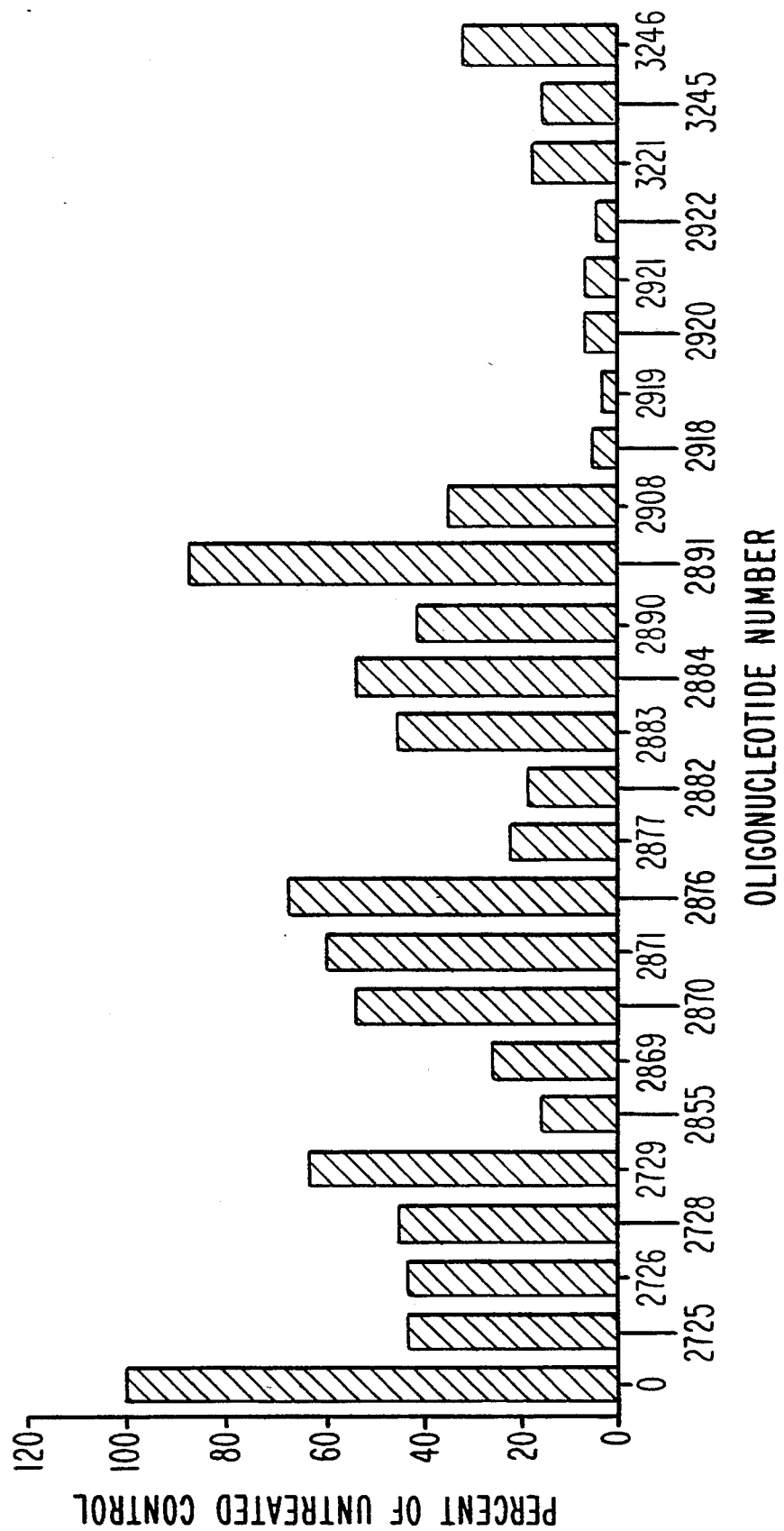
FIG. 1 is a bar graph showing the antiviral activity of oligonucleotides 2725 through 3246 against cytomegalovirus.

Antisense oligonucleotides hold great promise as therapeutic agents for the treatment of many human diseases. Oligonucleotides specifically bind to the complementary sequence of either pre-mRNA or mature mRNA, as defined by Watson-Crick base pairing, inhibiting the flow of genetic information from DNA to protein. Numerous recent studies have documented the utility of antisense oligonucleotides as biochemical tools for studying target proteins. Rothenberg st. al., *J. Natl. Cancer Inst.* 1989, 81, 1539–1544; Zon, G. *Pharmaceutical Res.* 1987, 5, 539–549. Because of recent advances in oligonucleotide chemistry, synthesis of nuclease-resistant oligonucleotides, and availability of types of oligonucleotides which exhibit enhanced cell uptake, it is now possible to consider the use of antisense oligonucleotides as a novel form of therapeutics.

For therapeutics, an animal suspected of having a cytomegalovirus infection is treated by administering oligonucleotides in accordance with this invention. Persons of ordinary skill can easily determine a therapeutically effective amount and optimum dosages, dosing methodologies and repetition rates. Such treatment is generally continued until either a cure is effected or a diminution in the disease state is achieved.

It is to be expected that differences in the DNA of cytomegalovirus from different species and from different types within a species exist. Thus, it is believed, for example, that the regions of the various cytomegalovirus species serve essentially the same function for the respective species and that interference with expression of the genetic information will afford similar results in the various species. This is believed to be so even though differences in the nucleotide sequences among the species doubtless exist.

Accordingly, nucleotide sequences set forth in the present specification will be understood to be representational for the particular species being described. Homologous or analogous sequences for different species of cytomegalovirus are specifically contemplated as being within the scope of this invention.

The present invention employs oligonucleotides for use in antisense inhibition of the function of cytomegalovirusRNA. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2-NH-O-CH_2$, $CH_2-N(CH_3)-O-CH_2$, $CH_2-O-N(CH_3)-CH_2$, $CH_2-N(CH_3)-N(CH_3)-CH_2$ and $O-N(CH_3)-CH_2-CH_2$ backbones (where phosphodiester is $O-P-O-CH_2$). Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group.

The oligonucleotides in accordance with this invention preferably comprise from about 5 to about 50 nucleic acid base units. It is more preferred that such oligonucleotides comprise from about 8 to 25 nucleic acid base units, and still more preferred to have from about 12 to 25 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a transcription initiation site, a translation initiation site, an intron/exon junction or sequences in the 5'- or 3'-untranslated region or 5' cap region.

The human CMV genome is the most complex of the herpes viruses in terms of its genomic structure. Replication-defective mutants of human CMV have only been isolated for two viral genes, the immediate early complex (IE1 or IE2) and the DNA polymerase. These genes are known to play major roles in human CMV gene expression. They have been selected as primary targets for antisense compound design. Secondary target genes for the design of therapeutic antisense oligonucleotides have been selected by analogy to genes of herpes simplex virus. Such genes have been determined to be essential for herpes simplex virus replication and/or sensitive to antisense inhibition. Four gene products of herpes simplex virus which have recently shown to be sensitive to antisense inhibition are the virion tegument protein (UL48), the two proteins constituting the ribonucleotide reductase enzyme (UL39, 40) and a virion phosphotransferase (UL13). Other herpes simplex virus genes which are currently being studied are the auxiliary DNA replication enzymes (UL5, 8, 9, 29, 42, 52) and the major capsid protein (UL36). CMV encodes proteins which have been identified as potentially analogous in function to each of these herpes simplex virus proteins; these genes have been selected to serve as secondary targets in connection with this invention.

The molecular biology of immediate early transcription in CMV has been as well elucidated as that of any transcriptional unit in the eucaryotic cell. Briefly, synthesis of the major immediate early transcript (IE1) is controlled by a number of repeat units 5' of the mRNA cap site. These repeats are responsive to a number of transcriptional response molecules known to operate in cell-specific and differentiation specific manners. The IE1mRNA is an abundant RNA which is 1.9 kb in length and encodes a protein which migrates with an apparent molecular weight of 72 kDa on PAGESDS. This protein has been found in virions and controls the expression of itself as well as that of the IE2 gene product. At the initial phase of immediate early transcription, only IE1 mRNA is synthesized by the cellular RNA polymerase. A small amount of IE2 mRNA is made by processing of the IE1mRNA during this early time of infection. Over time, levels of IE1 protein accumulate and bind the promoter region of the IE1 gene, repressing further transcription of the IE1 mRNA and allowing a weaker downstream promoter for the IE2 gene to control further synthesis of IE2 mRNA. It has been proposed that the IE1 gene product may serve to boost viral transcription during a productive infection and alternatively to activate viral gene expression from the latent state. The observation of cell-type and differentiation or hormonal responsive elements in the promoter of the IE1 gene are consistent with this proposition. The IE2 protein is capable of transcriptionally activating many of the CMV early and late genes in a manner similar to other known transactivating proteins of cellular and viral origin. Thus, the IE2 protein is believed to be one of the master switches for CMV gene expression. The other controlling switch of CMV genes is the DNA polymerase protein. Transcription of the late viral genes operates at very low levels until the onset of viral DNA replication, after which the late genes are activated by an increased template availability. The exact molecular condition which is operant in this enhanced template availability is unclear, but the presence of the viral DNA polymerase and replication of the genome are essential requirements for the observed effect.

The selected targets within the mRNA sequences include regions of the mRNA which are known to control mRNA stability, processing and/or translational efficiency. These target sites include the 5' cap regions and translation initiation control regions. The target sequences for the IE1, IE2, and DNA polymerase genes are set forth in Table 1:

TABLE 1

| TARGET SEQUENCES FOR CYTOMEGALOVIRUS Oligonucleotide Synthesis | | | |
|---|---|---|---|
| TARGET GENE | TARGET REGION | TARGET DNA SEQUENCE | SEQ ID NO |
| DNA POLYMERASE | mRNA CAP SITE | GGACCGGGACCACCGTCGTC | 65 |
| DNA POLYMERASE | AUG REGION | GTCCGCTATGTTTTTCAACCC | 66 |
| DNA POLYMERASE | CONSERVED AA (717-732) | CCTTCCATCATCATGGCCCAC | 67 |
| DNA POLYMERASE | CONSERVED AA (905-914) | GGCGCGGGTCATCTACGGGAC | 68 |
| DNA POLYMERASE | CMV INSERTION (608-697) | CCGCTGTGCCCGGCGACGCGG | 69 |
|  |  | CCGCCCTTGCAATCTGCGCCG | 70 |
|  |  | GGCGTTTCACCCGGCTCCGGC | 71 |
| DNA POLYMERASE | (1109-1159) | GCGCCCGGTGTCCGGACGGCG | 72 |
|  |  | CCGCCGGCGTGGTTTCCCGGT | 73 |
|  |  | CCGGCAAAGAAGAGGGCGCGG | 74 |
| IE1 | mRNA CAP SITE | GTGAACCGTCAGATCGCCTGG | 75 |
| IE1 | AUG REGION | CTTGACACGATGGAGTCCTC | 76 |
| IE1 | I/E-1 | GCCAAGAGTGACGTAAGTACC | 77 |
| IE1 | I/E-2 | GTCTTTTCTGCAGTCACCGTC | 78 |
| IE1 | I/E-3 | CAAGGTGCCACGGTACGTGTC | 79 |
| IE1 | I/E-4 | CATGTGTTTAGGCCCGAGAC | 80 |
| IE1 | I/E-5 | GGCAGAACTCGGTAAGTCTG | 81 |
| IE1 | I/E-6 | CCTCCTCTACAGTCAAACAG | 82 |
| IE2 | AUG/CAP SITE | GCGCCTATCATGCTGCCCCTC | 83 |
| IE2 | AUG REGION | GCTCTCCAGATGAACCACCC | 84 |
| IE2 | I/E-1 | CAAGATTGACGAGGTGAGCCG | 85 |
| IE2 | I/E-2 | CCCAAACAGGTCATGGTGCGC | 86 |
| IE2 | NUC SIG-1 | GCGTAAGAAACCGCGCAAAAC | 87 |

TABLE 1-continued

TARGET SEQUENCES FOR CYTOMEGALOVIRUS
Oligonucleotide Synthesis

| TARGET GENE | TARGET REGION | TARGET DNA SEQUENCE | SEQ ID NO |
|---|---|---|---|
| IE2 | NUC SIG-2 | CGCAAGAAGAAGAGCAAACGC | 88 |

In Table 1, the abbreviation I/E refers to the intron-/exon junction while the AUG region is the translation initiation region of IE2 mRNA whose transcription is controlled by the IE2 specific promoter region. The abbreviation "nuc sig" refers to nuclear localization signals of the IE2 protein.

Oligonucleotides useful in the invention are complementary to the DNA (especially for oligonucleotides directed to intron/exon junctions) or to the corresponding messenger RNA (mRNA) or pre-messenger RNA. Thus, the oligonucleotides in accordance with the invention preferably have one of the foregoing sequences or an effective portion thereof. Thus, it is preferred to employ any of these oligonucleotides as set forth above or any of the similar nucleotides which persons of ordinary skill in the art can prepare from knowledge of the preferred antisense targets for the modulation of the viral infection.

The oligonucleotides of this invention can be used in diagnostics, therapeutics and as research reagents and kits. For therapeutic use, the oligonucleotide is administered to an animal suffering from a cytomegalovirus infection. Oligonucleotides may be formulated in a pharmaceutical composition, which may include carriers, thickeners, diluents, buffers, preservatives, surface active agents and the like in addition to the oligonucleotide. Pharmaceutical compositions may also include one or more active ingredients such as antimicrobial agents, antiinflammatory agents, anesthetics, and the like in addition to oligonucleotide.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine a therapeutically effective amount and optimum dosages, dosing methodologies and repetition rates.

The present invention is also useful in diagnostics and in research. Since the oligonucleotides of this invention hybridize to nucleic acid from cytomegalovirus, sandwich and other assays can easily be constructed to exploit this fact. Provision of means for detecting hybridization of oligonucleotide with cytomegalovirus present in a sample suspected of containing it can routinely be accomplished. Such provision may include enzyme conjugation, radiolabelling or any other suitable detection systems. Kits for detecting the presence or absence of cytomegalovirus may also be prepared.

EXAMPLES

EXAMPLE I Cells and Virus

Human foreskin fibroblast (ATCC #CRL 1635) cells used are obtained from the American Tissue Culture Collection. Cultures are grown in Dulbecco's Modified Eagle's Medium with 4.5 g/L glucose (high glucose DMEM) and supplemented with 10% fetal bovine serum (FBS), penicillin (100 units/ml), streptomycin (100 micrograms/ml) and L-glutamine (2 mM). Stock cultures of human cytomegalovirus (human CMV strain AD169 or Towne) are grown on foreskin cells using low multiplicity infections (multiplicity of infection [MOI]=0.02 plaque forming units [PFU]/cell).

To assess the ability of oligonucleotides to inhibit CMV replication, an infectious yield assay will be used. To perform this assay, foreskin cells are seeded at a density of $5 \times 10^5$ cells per well in Falcon 6 well tissue culture plates. Cells are overlaid with 2 ml of medium (high glucose DMEM with 10% FBS) and incubated at 37° C. for 18–24 hours. Where appropriate, cells are overlaid with oligonucleotide preparations in 1 ml of medium at 24 hours after seeding the plates. Following an 18 hour incubation, all wells are rinsed with phosphate buffered saline and infected with CMV at varying MOIs suspended in 0.5 ml of serum-free hgh glucose DMEM. Virus and cells are incubated at 37° C. for 90 minutes on a rocking platform. Following viral adsorption, unadsorbed virus is rinsed away by washing with phosphate buffered saline. Where appropriate, 1 ml of medium (high glucose DMEM with 10% FBS) containing 10 µM concentrations of oligonucleotide are added to the well and the cells are incubated for 4–5 days at 37° C. Control wells receive 1 ml of medium which contains no oligonucleotide.

Virus is harvested into the overlay medium and triplicate wells of each experimental point are combined. The suspension is frozen at −80° C. Virus titer is determined for each sample by plaque assay on human foreskin cell monolayers. Dilutions of each virus preparation are prepared and duplicate aliquots of each dilution are absorbed onto foreskin cells for 90 minutes with rocking. After adsorption, the unadsorbed virus inoculum is removed by rinsing the plates with phosphate buffered saline and the cells are overlaid with 2 ml of high glucose DMEM containing 5% FBS and 0.75% methyl cellulose. Cells are incubated at 37° C. for 12–14 days before plaques are fixed with formalin, stained with crystal violet and counted. Plaque counts from treated wells are compared with those from the control wells to establish the degree of inhibition of infectious virus production.

It is anticipated that treatment of CMV-infected cells with 10 μM concentrations of phosphorothioate oligonucleotides which exhibit sequence complementarity to the CMV IE1, IE2 or DNA polymerasemRNAs will reduce the infectious yield of virus by 90%.

EXAMPLE 2

The mechanism of action of active CMVantisense compounds can also be validated. The molecular nature of any mechanism of action study is dictated by the CMV gene sequence which is the target of oligonucleotide inhibition. The most direct assays take advantage of the biological function of the protein encoded by the target CMVgene. The biological activity of an enzymatic protein often amplifies the end signal of such an assay so that the assay is very sensitive to even small changes in viral protein levels. Examples of CMV genes which are amenable to these types of assays are the DNA polymerase and IE1 & 2 loci.

For the DNA polymerase protein, a simple mechanistic assay involves assessing the ability of target specific oligonucleotides to inhibit the incorporation of $^3$H-thymidine into viral DNA under conditions which favor viral DNA polymerase activity over cellular DNA polymerase activity. The ability of the CMV IE proteins to transactivate RNA synthesis of certain CMV genes has been used to devise a transient gene expression assay, whose activity depends upon the presence of biologically active IE1 or IE2 proteins in an infected cell. Briefly, IE1 or IE2 responsive promoter regions are cloned 5' of an indicator gene (e.g., bacterial chloramphenicol acetyl transferase, CAT) in a plasmid vector. The vector is introduced into human foreskin cells, which in turn are infected with human CMV. The detection of CAT activity can be determined from cell lysates and CAT activity levels used to indirectly quantitate IE1 or IE2 protein levels. The effect of oligonucleotides on the CAT activity will be compared for both the IE1 and IE2 responsive constructs.

In cases in which an overt biological activity is not easily demonstrable, oligonucleotide-induced changes in protein levels can be determined by immunoprecipitation of infected cell proteins, gel electrophoresis of the immunoprecipitate in an SDS-acrylamide matrix, and detection of target protein levels by autoradiography of the gel. Proteins of assayable biological activity can also be quantitated by immunoprecipitation and gel electrophoretic techniques.

EXAMPLE 3

The value of a CMVantisense drug will in a large degree depend on its ability to specifically interact with CMV RNA targets without adversely effecting host cell functions. Therefore it is important to evaluate the potential for nonspecific interactions and toxicities of active compounds. The potential for these adverse reactions is accessed in numerous models of acute and chronic cellular toxicity. Initially, active compounds are evaluated for toxicity in infected human foreskin cells using $^3$H-leucine and $^3$H-thymidine to measure effects on protein and DNA synthesis, respectively. From determinations of the oligonucleotide LD50 in these assays and the ID50 activity values obtained in the primary and secondary activity screens, a therapeutic index (T.I.) for each active oligonucleotide compound is determined. Only those compounds exhibiting T.I. more than 100 are then considered for subsequent evaluation.

EXAMPLE 4 Synthesis and characterization of oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropylphosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

2'-O-methyl phosphorothioate oligonucleotides were synthesized using 2'-O-methyl β-cyanoethyldiisopropylphosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide. 2'-O-propyl phosphorothioate oligonucleotides were prepared as disclosed in U.S. patent application Ser. No. 566,977, filed Aug. 13, 1990, which is assigned to the same assignee as the instant application and which is incorporated by reference herein.

2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, pH 7.0. Oligodeoxynucleotides and phosphorothioate oligonucleotides were judged from electrophoresis to be greater than 80% full length material.

EXAMPLE 5

ELISA assay for inhibition of CMV replication by antisense oligonucleotides

Oligonucleotides complementary to human cytomegalovirus mRNA were tested for antiviral activity in an ELISA-based assay of CMVreplication. Normal human dermal fibroblasts (Clonetics Corp., San Diego Calif.) were grown in serum-free medium (Clonetics) and used to seed 96-well plates. When cells are approximately 80% confluent, they are pretreated with oligonucleotides. Approximately 20 hours after pretreatment the medium (containing oligonucleotides) is carefully poured off and the cells washed twice with warmed fibroblast basal medium (FBM, Clonetics). Cells are then infected with 100 μl/well of CMV stock diluted in FBM. The plates are incubated at 37° C. for two hours. The medium (containing virus) is then carefully poured off and replaced with fresh, prewarmed FBM medium, 100 μl per well. The plates are briefly incubated at 37° C. and then 5 μl of oligonucleotide, diluted in FBM, is reintroduced into the medium in each well. Two days later, cells are post-treated again with oligonucleotides in the same way. On day six, the plates are prepared for ELISA.

In preparation for ELISA, the medium is carefully poured off the plates, and cells are fixed in 200 μl of absolute ethanol per well. Cells are fixed for 30 minutes at room temperature, then ethanol is removed and plates are air-dried. Plates are blocked for one hour prior to ELISA with PBS containing 2% BSA. Blocking solution is removed and 100 μl of an anti-CMV antibody, diluted 1:2000 in PBS with 1% BSA, is added. Cells are incubated in antibody for one hour at 37° C. and washed three times in PBS. The secondary antibody, biotinylated goat anti-mouse IgG (Bethesda Research Labs, Md.), is diluted 1:1000 in PBS with 1% BSA, and incubated with cells for one hour at 37° C. Cells are then washed and incubated for one hour at 37° C. in streptavidin-B-D-galactosidase. Color is developed with chlorophenol red-B-D-galactopyranoside, 20 mg dissolved in 10 ml of 50 mMNa Phosphate, 1.5 mMMgCl2; plates are shaken for 10 minutes and the absorbance is read at 575 nm.

Twenty-four oligonucleotides complementary to human CMV were tested for antiviral activity. The sequences and gene targets for these oligonucleotides are presented in Table 2.

from messenger RNA, which is transcribed from a common promoter, eight of these compounds are complementary to both the IE1 and IE2 mRNA. Three compound are complementary only to the IE1 and IE2 mRNA. Three compounds are complementary only to the IE1mRNA, and the remaining five are specific for IE2 mRNA.

At a screening concentration of 5 μM all of the phosphorothioate oligonucleotides demonstrated some reduction of virus replication relative to untreated cells (FIG. 1). Five oligonucleotides showed greater than 90% inhibition of virus at this concentration. These oligonucleotides (ISIS 2918, SEQ ID NO: 18; ISIS 2919, SEQ ID NO: 19; ISIS 2920, SEQ ID NO: 20; ISIS 2921, SEQ ID NO: 21; ISIS 2922, SEQ ID NO: 22) are preferred embodiments of the invention.

Figure 2:
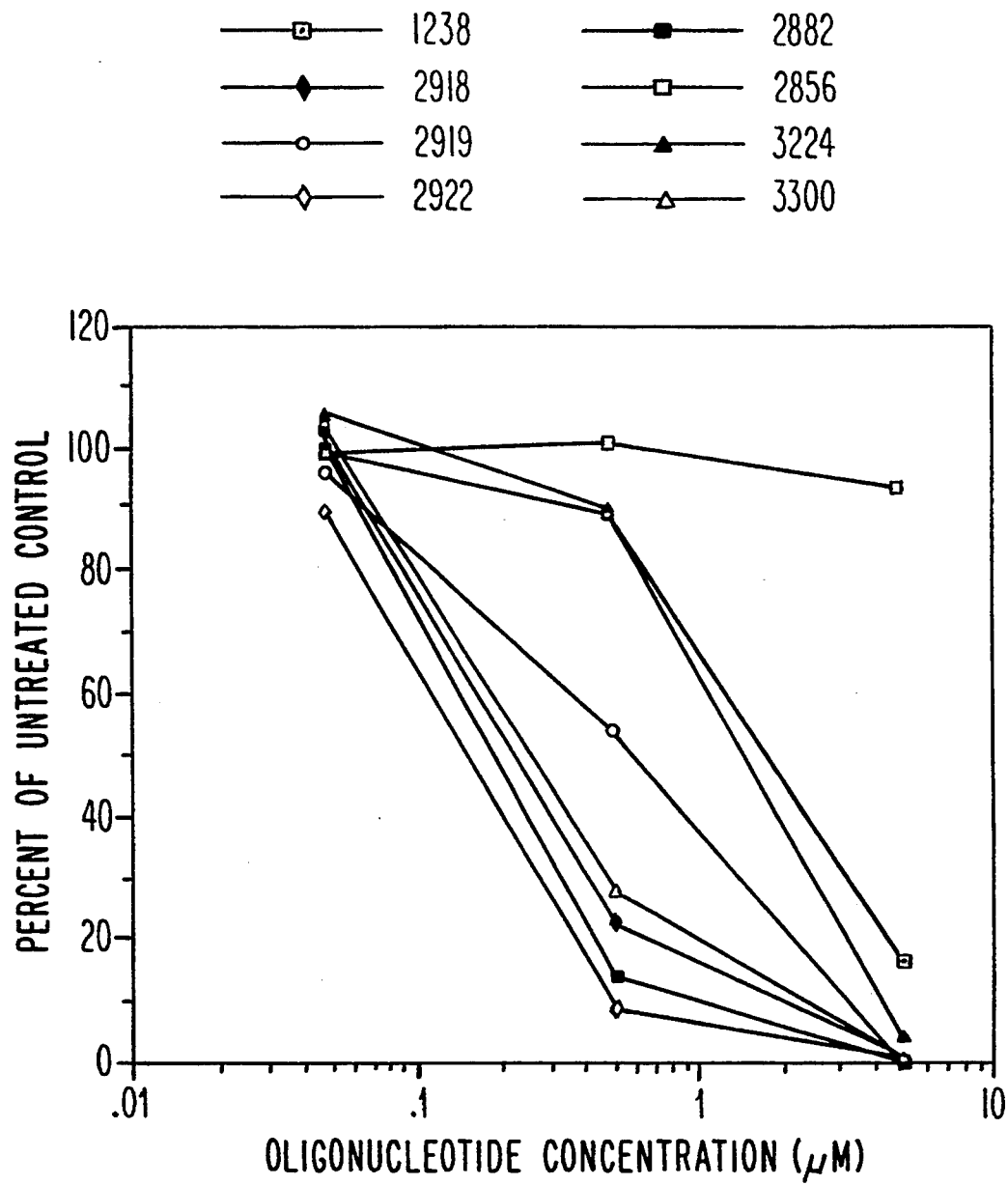
FIG. 2 is a line graph showing antiviral effects of eight oligonucleotides at doses from 0.01 to 10 $\mu$M.
Figure 3:
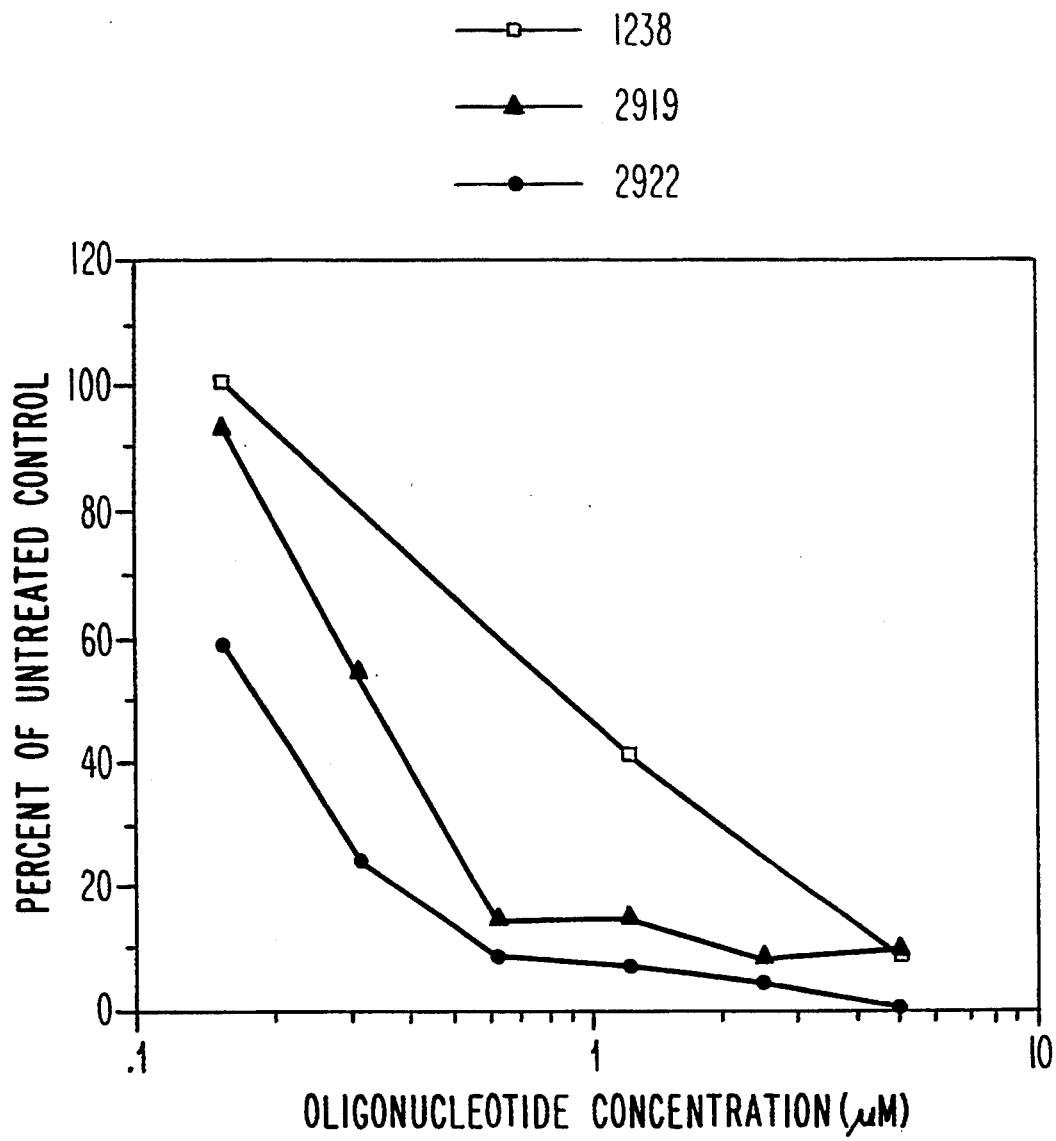
FIG. 3 is a line graph showing antiviral effects of three oligonucleotides at doses from 0.1 to 10 $\mu$M.

Dose-response experiments differentiated between nonspecific effects and sequence-specific inhibition of CMV replication by antisense oligonucleotides. Compounds ISIS 2922 (SEQ ID NO: 22), ISIS 2882 (SEQ ID NO: 12), ISIS 2918 (SEQ ID NO: 18), ISIS 2919 (SEQ ID NO: 19) and ISIS 3300 (SEQ ID NO: 24, P=S/2'-O-Me) all showed inhibition of CMV replication at lower doses than randomized oligonucleotides with no complementarity to CMV (FIG. 2). These oligonucleotides are preferred. Compounds ISIS 2918 (SEQ ID NO: 18), ISIS 2919 (SEQ ID NO: 19), and ISIS 2922 (SEQ ID NO: 22) are complementary to IE2 RNA sequences. ISIS 2882 (SEQ ID NO: 12) and ISIS 3300 (SEQ ID NO: 24, P=S and 2'-O-Me) are complementary to the 5' cap region of IE1 and IE2 transcripts. The activity of ISIS 2919 and ISIS 2922 relative to a randomized control oligonucleotide was confirmed in an independent dose-response experiment (FIG. 3).

TABLE 2

Oligonucleotides Tested for Activity Against CMV

| SEQ ID NO | ISIS # | NUCLEOTIDE #s | TARGET | SEQUENCE | TYPE |
|---|---|---|---|---|---|
| 1 | 2725 | | Nonsense | GTG TCA AGT GGC ACC ATA CG | P=S |
| 2 | 2726 | | Nonsense | TGG AAA GTG TAC ACA GGC GAA | P=S |
| 3 | 2728 | 80618–80639 | DNA pol. AUG | GGG TTG AAA AAC ATA GCG GAC | P=S |
| 4 | 2729 | 172755–172776 | IE1 AUG | GAG GAC TCC ATC GTG TCA AG | P=S |
| 5 | 2855 | 78445–78466 | DNA pol. coding | GTG GGC CAT GAT GAT GGA AGG | P=S |
| 6 | 2856 | 77903–77924 | DNA pol. coding | GTC CCG TAG ATG ACC CGC GCC | P=S |
| 7 | 2869 | 78688–78709 | DNA pol. coding | CGG CGC AGA TTG CAA GGG CGG | P=S |
| 8 | 2870 | 78655–78676 | DNA pol. coding | GCC GGA GCC GGG TGA AAC GCC | P=S |
| 9 | 2871 | 77305–77326 | DNA pol. coding | CGC CGT CCG GAG ACC GGG CGC | P=S |
| 10 | 2876 | 77250–77271 | DNA pol. coding | ACC GGG AAA CCA CGC CGG CGG | P=S |
| 11 | 2877 | 77155–77176 | DNA pol. coding | CCG CGC CCT CTT CTT TGC CGG | P=S |
| 12 | 2882 | 173601–173622 | IE1 int/exon 1 | GGT ACT TAC GTC ACT CTT GGC | P=S |
| 13 | 2883 | 172775–172796 | IE1 int/exon 2 | GAC GGT GAC TGC AGA AAA GAC | P=S |
| 14 | 2884 | 172686–172707 | IE1 int/exon 3 | GAC ACG TAC CGT GGC ACC TTG | P=S |
| 15 | 2890 | 172572–172592 | IE1 int/exon 4 | GTC TCG GGC CTA AAC ACA TG | P=S |
| 16 | 2891 | 172387–172407 | IE1 int/exon 5 | CAG ACT TAC CGA CTT CTG CC | P=S |
| 17 | 2908 | 172218–172238 | IE1 int/exon 6 | CTG TTT GAC TGT AGA GGA GG | P=S |
| 18 | 2918 | 170373–170394 | IE2 AUG | GGG TCC TTC ATC TGG GAG AGC | P=S |
| 19 | 2919 | 170004–170025 | IE2 int/exon 1 | CGG CTC AGG TCG TCA ATC TTG | P=S |
| 20 | 2920 | 169535–169556 | IE2 int/exon 2 | GCG CAC CAT GAC CTG TTT GGG | P=S |
| 21 | 2921 | 170652–170673 | IE2 nuc sig 1 | GTT TTG CGC GGT TTC TTA CGC | P=S |
| 22 | 2922 | 170120–170141 | IE2 nuc sig 2 | GCG TTT GCT CTT CTT CTT GCG | P=S |
| 23 | 3245 | 173713–173734 | IEI/IE2 5' cap | CGT CTC CAG GCG ATC TGA CGC | P=S |
| 24 | 3246 | 173710–173731 | IE1/IE2 5' cap | TGG CGT CTC CAG GCG ATC TGA | P=S |
| | 3258 | " " | " " | " " | 2'-O—Me |
| | 3300 | " " | " " | " " | P=S/2'-O—Me |
| 25 | 3224 | | Random | TCT GAG TAG CAG AGG AGC TC | P=S/2'-O—Me |
| 26 | 3221 | | Random | CTC CAG GCG AAT TTT AAC ACA | P=S |
| | 3266 | | " " | " " | 2'-O—Me |
| 27 | 1238 | | Random | ACT CGG GCT GCC ACT GAA CAG | P=S |

Of the oligonucleotides tested, eight were complementary to mRNA encoding the human CMV DNA polymerase, and the remainder were complementary to RNA transcribed from the major immediate early promoter of CMV. Since the two major protein products from this genomic region (IE1 and IE2) are synthesized

EXAMPLE 6

Comparison of ISIS 2918 and ISIS 2922 to ganciclovir (DHPG)

The antiviral activity of oligonucleotides 2918 and 2922 was compared to the antiviral activity of ganciclovir (DHPG) in dose-response experiments using the ELISA assay described in Example 5, with either ganciclovir or oligonucleotide being added after infection with virus. Both oligonucleotides demonstrated potent antiviral activity, with $EC_{50}$s (50% effective concentration, the concentration needed to give 50% inhibition) against the AD 169 strain of human CMV of 0.1 μM for ISIS 2922 and 0.25 μM for ISIS 2918. The $EC_{50}$ for ganciclovir in this experiment was 3 μM, demonstrating that ISIS 2922 was approximately 30 fold more potent than ganciclovir on a molar basis.

Similar results were obtained when the antiviral activity of 2922 and ganciclovir was determined for the Towne strain of human CMV.

EXAMPLE 7 Plaque reduction assay

Six-well culture plates were seeded with NHDF cells at a density of 500,000 cells per well in serum-free FGM. Subconfluent monolayers were pretreated with oligonucleotides overnight, and then rinsed three times to remove residual oligonucleotide prior to virus infection. Human CMV in FGM was added to cells at a dilution sufficient to result in the formation of approximately 100 plaques per well in untreated cells. After a two-hour adsorption, virus was removed and cells were overlaid with a 1:1 mixture of 1% Seaplaque agarose (FMC) and 2X minimal essential medium. Duplicate samples were counted and the mean expressed as the percent of plaques which developed in untreated cells.

Figure 4:
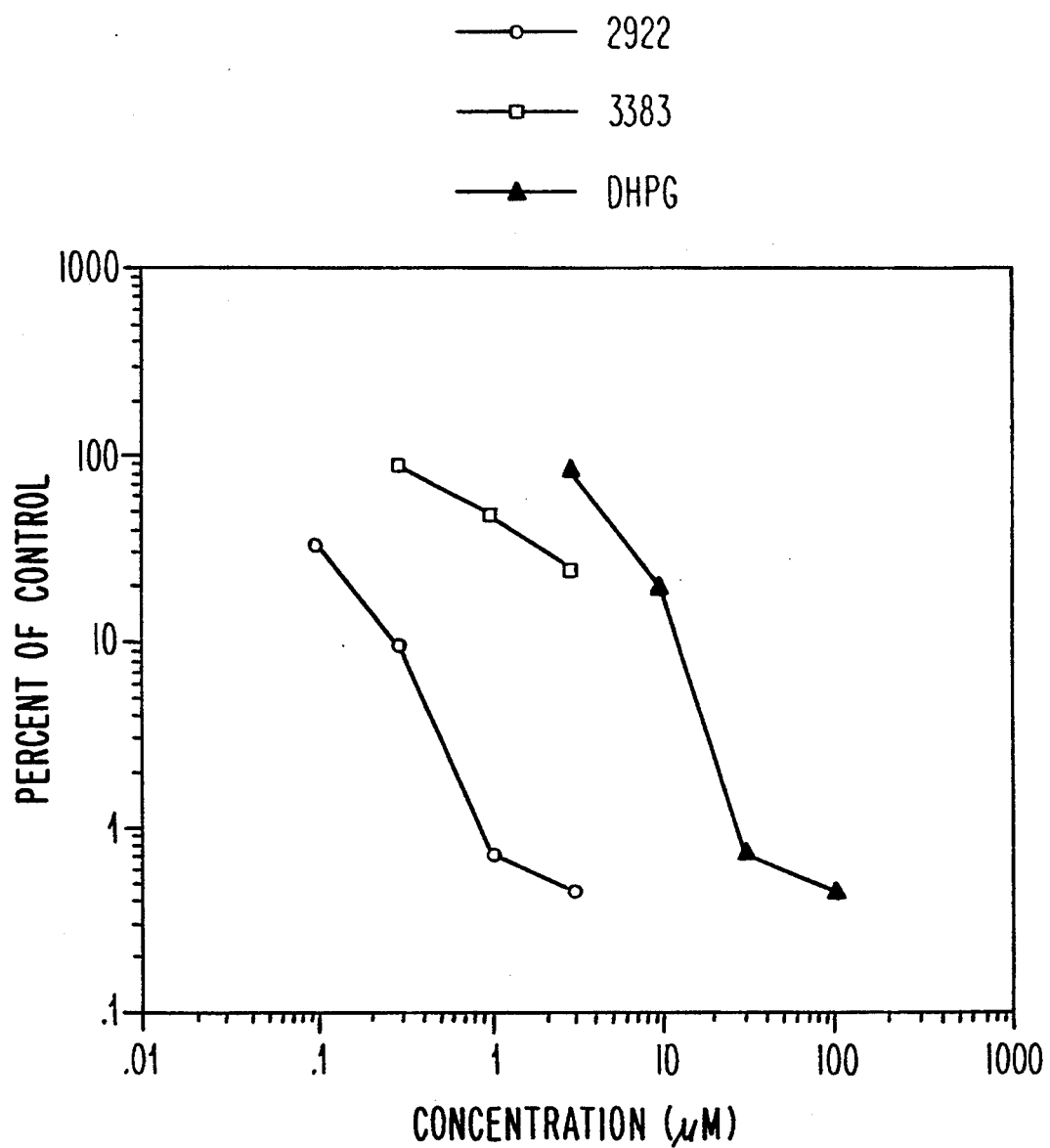
FIG. 4 is line graph showing dose-response curves of ISIS 2922, ISIS 3383 (negative control) and ganciclovir (DHPG) activity against human CMV plaque formation.

Treatment of host cells with ISIS 2922 reduced the ability of human CMV to form plaques on monolayers of NHDF cells (FIG. 4). At a concentration of 1 μM plaque formation was inhibited by greater than 99%.

EXAMPLE 8

Yield reduction assay

Six-well culture plates were seeded with NHDF cells at a density of 500,000 cells per well in serum-free FGM or FGM containing 0.2% FBS. Subconfluent monolayers were pretreated with oligonucleotides overnight. After rinsing cells three times to remove residual oligonucleotide, virus in FGM was added and allowed to adsorb for two hours. Virus was then removed and cells were overlaid with fresh medium containing oligonucleotide. For evaluation of total virus yield, infected cells were incubated for 8 days, scraped into the culture supernatant and stored frozen at −80° C.

Infectious virus yield from harvested samples was determined in duplicate by standard plaque assay on monolayers of NHDF cells. An agarose overlay consisting of a 1:1 mixture of 1% Seaplaque agarose (FMC) and 2X minimal essential medium was applied to cells after adsorption. Following incubation for 8 days, cells were fixed in formaldehyde and stained overnight with methylene blue in phosphate buffered saline.

The ability of ISIS 2922 to inhibit production of infectious human CMV in NHDF cells was determined using the yield reduction assay. 90% and 99% inhibition of infectious virus production was achieved at 1.2 μM and 2.2 μM concentrations of ISIS 2922, respectively, when evaluating combined extracellular and intracellular virus yield. In contrast, 90% and 99% inhibition of CMV production by ganciclovir was only achieved at concentrations of 16 μM and 36 μM, respectively. A control oligonucleotide, ISIS 3383, showed no inhibition of infectious CMV yield at doses up to 3 μM.

EXAMPLE 9

Reduced expression of human CMV immediate early proteins in ISIS 2922-treated cells The steady-state levels of immediate early proteins in CMV-infected NHDF cells were examined using western blot analysis. Subconfluent monolayers of NHDF cells in six-well culture plates were treated with oligonucleotide and infected as described in Example 8. Forty-eight hours after infection, medium was aspirated and cells were scraped into 200 μl of lysis buffer (20 mM Tris-HCl, pH 7.5; 20 mM KCl; 5 mM EDTA; 1% Triton X-100; 0.1 mM leupeptin; 10 μg/ml aprotinin). After pelleting nuclei and debris (15,000×g for 10 minutes), the supernatant was transferred to a fresh tube, and protein from a 10 μl sample was fractionated by electrophoresis on a denaturing sodium dodecyl sulfate, 8% polyacrylamide gel under reducing conditions. Fractionated proteins were transferred electrophoretically to nitrocellulose membranes and IE1 and IE2 polypeptides were detected using a mouse monoclonal antibody (MAB810, Chemicon, Temecula, Calif.) which recognizes a shared epitope on both IE1 and IE2 proteins. Alkaline phosphatase-conjugated goat anti-mouse IgG was used as a secondary antibody, and blots were developed in NBT and BCIP (BRL Gibco, Gaithersburg, Md.).

Figure 5A:
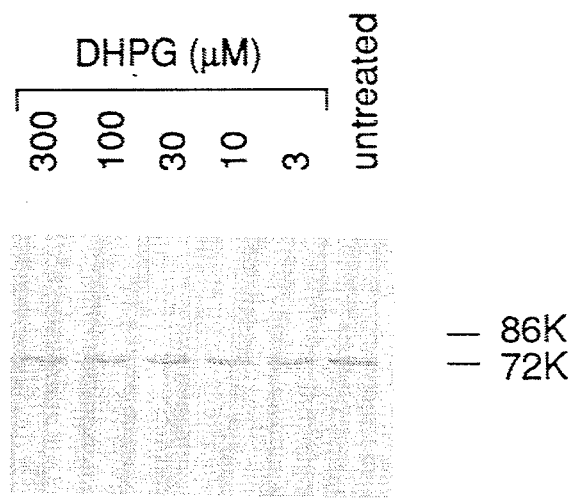
FIG. 5 is a photograph of a Western blot showing inhibition of expression of CMV immediate early protein products by ISIS 2922, ISIS 3383 (negative control) and ganciclovir (DHPG).
Figure 5B:
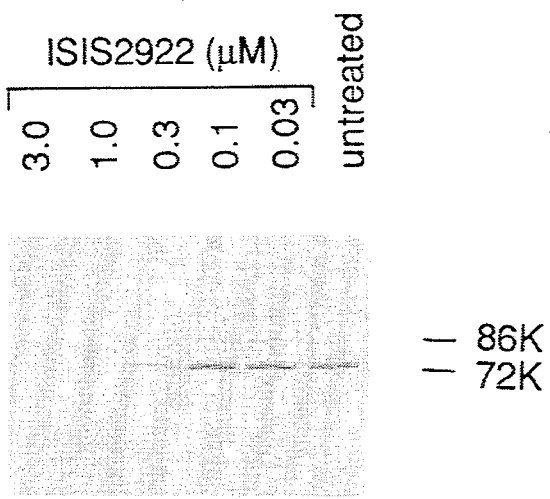
Figure 5C:
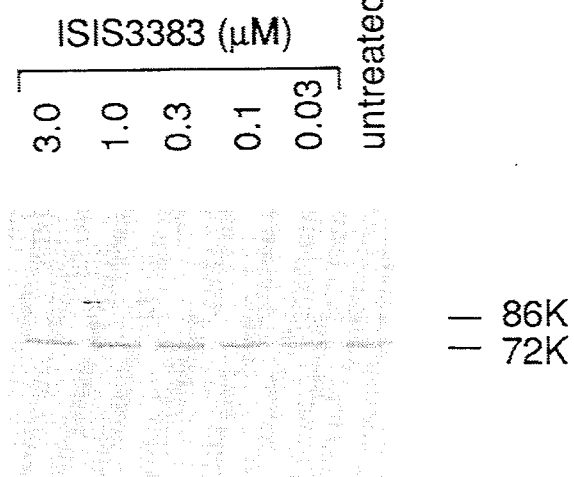

FIG. 5 demonstrates the effect of oligonucleotide 2922 treatment on immediate early protein levels. The levels of both immediate early polypeptides were reduced in CMVinfected cells treated with ISIS 2922. Both proteins were significantly reduced after treatment with 0.3 μM oligonucleotide, and were undetectable in cells treated with 1 μM oligonucleotide.

The ability of ISIS 2922 to inhibit expression of immediate early proteins was confirmed qualitatively using immunofluorescent staining of human CMV-infected cells. Subconfluent NHDF cells in wells of a four-chamber culture slide (Costar) were pretreated with oligonucleotide overnight (15-20 hours), infected with human CMV using a M.O.I. of 3 pfu/cell, treated for an additional 24 hours at 37° C., and fixed in ethanol at −20° C. Immediate early proteins were detected using the same monoclonal antibody, MAB810, used for Western blot analysis, and rhodamine-conjugated goat antimouse IgG. Cells were examined and photographed using a Nikon epifluorescence microscope.

After treatment with ISIS 2922 at a concentration of 1 μM, the number of cells exhibiting the nuclear immunofluorescence characteristic of human CMV-infected cells 24 hours after infection was reduced to less than 10%, compared to over 70% for control cells not treated with oligonucleotide. The intensity of fluorescence was also reduced in oligonucleotide-treated cells.

EXAMPLE 10

Activity of oligonucleotides having sequences related to that of ISIS 2922

Oligonucleotides having the sequence of ISIS 2922 but with one or more nucleotide substitutions creating mismatches at internal sites were tested against human CMV in the ELISA assay described in Example 5.

Figure 6:
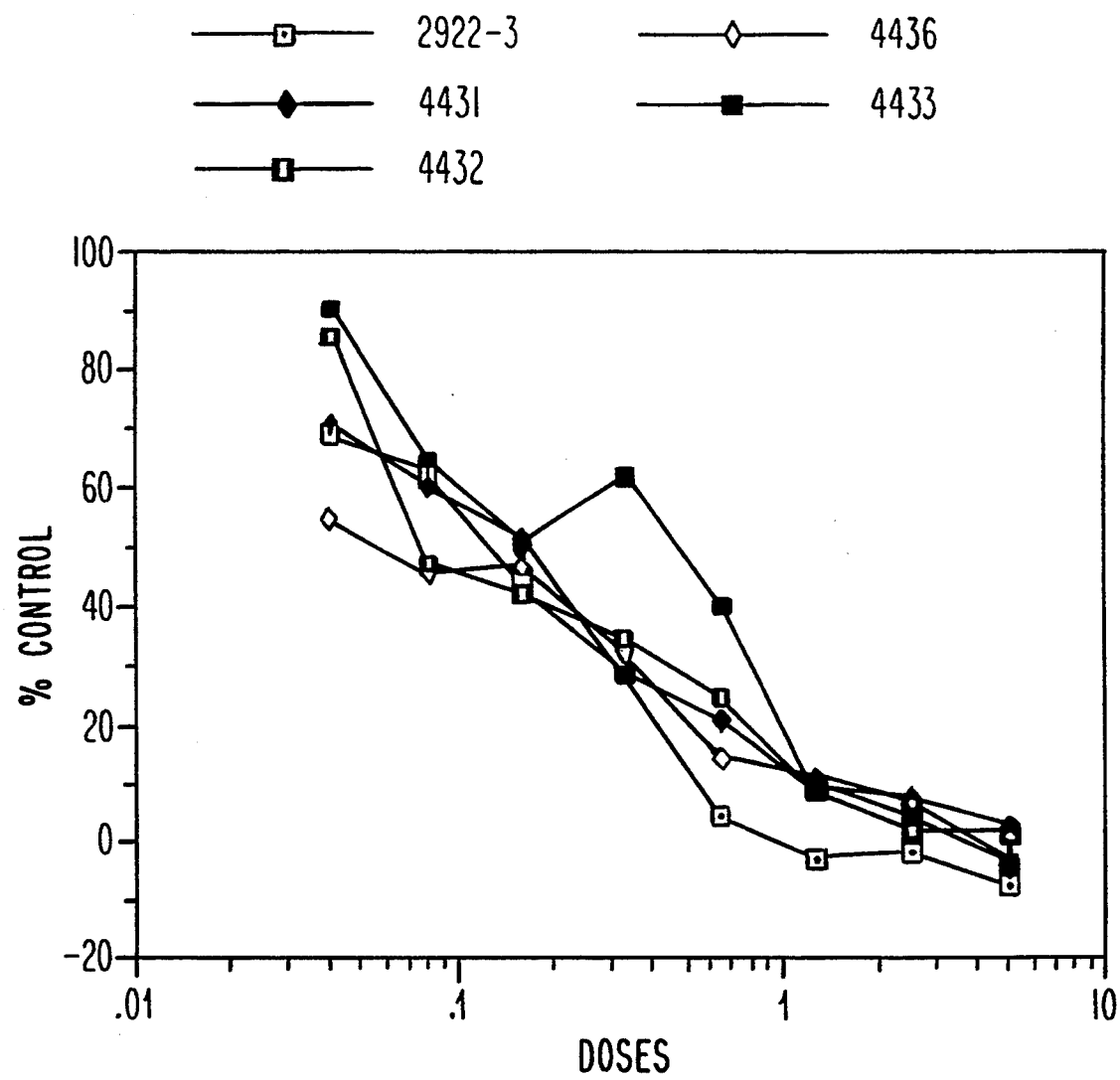
FIG. 6 is a line graph showing dose response curves of ISIS 2922 and variants of this sequence with base mismatches (ISIS 4431, 4432, 4436, 4433).

Surprisingly, it was found that up to four internal mismatches could be tolerated without loss of antiviral activity, although the Tm (melting temperature) measured for these oligonucleotides hybridized with the RNA complement of ISIS 2922 was significantly reduced with each mismatch. This is shown in FIG. 6. In contrast, a 19-mer with the same sequence as 2922, but with one nucleotide removed from each end (ISIS 4376) was inactive in the ELISA assay at concentrations up to 5 µM. An oligonucleotide (17-mer) with a further nucleotide removed from each end was also inactive. These oligonucleotides and their activity against CMV are shown in Table 3. Oligonucleotides displaying activities at least 50% that of control (ISIS 2922) as shown in Table 3 or FIG. 6 are preferred.

TABLE 3

Effect of oligonucleotide length and sequence on activity against human CMV

| ISIS # | SEQUENCE | ACTIVITY | Tm (°C.) | SEQ ID NO: |
|---|---|---|---|---|
| 2922 | GCGTTTGCTCTTCTTCTTGCG | 100 | 54.6 | 22 |
| 4376 | -CGTTTGCTCTTCTTCTTGC- | <10 | N.D. | 28 |
| 4367 | --GTTTGCTCTTCTTCTTG-- | <10 | 49.1 | 29 |
| 5476 | GCGTTTGCTCTTCTTCTTGC- | 40 | 52.4 | 30 |
| 5478 | GCGTTTGCTCTTCTTCTTG-- | 33 | 50.6 | 31 |
| 5479 | GCGTTTGCTCTTCTTCTT--- | 20 | N.D. | 32 |
| 5480 | GCGTTTGCTCTTCTTCT---- | 21 | N.D. | 33 |
| 5477 | -CGTTTGCTCTTCTTCTTGCG | 38 | 53.1 | 34 |
| 5481 | --GTTTGCTCTTCTTCTTGCG | 53 | 53.2 | 35 |
| 5482 | ---TTTGCTCTTCTTCTTGCG | 35 | N.D. | 36 |
| 5483 | ----TTGCTCTTCTTCTTGCG | 47 | N.D. | 37 |
| 4431 | GCGTTTGCTCCTCTTCTTGCG | 83 | 48.4 | 38 |
| 4432 | GCGTTTTCTCTTCTGCTTGCG | 88 | 34.9 | 39 |
| 4433 | TCGGTTTCTCGTCTGCTTTCG |  | 24 | 40 |
| 4436 | GCGGTTTCTCTTCTGCTTTCG | — | | 41 |

Oligonucleotides are shown 5' to 3'. A hyphen indicates a deletion relative to ISIS 2922 sequence. Bold letters indicate changes (mismatches) with respect from ISIS 2922 sequence.

Antiviral activity is expressed as percent of ISIS 2922 activity, and is determined using the equation:

$$[EC_{50}(ISIS\ 2922)/EC_{50}(oligonucleotide)] \times 100$$

$T_m$ is determined against an RNA strand which is the exact complement of ISIS 2922.

Shifting the oligonucleotide target sequence to one side or the other from the 2922 target also affected activity. A 21-mer complementary to a sequence 4 bases downstream (toward the 3' end) of the 2922 target (ISIS 4377, SEQ ID NO: 42) was active in the ELISA assay, though higher doses were required than for 2922. In contrast, a 21-mer complementary to a sequence 4 bases upstream (toward the 5' end) of the 2922 target sequence (ISIS 4378, SEQ ID NO: 43) demonstrated activity at even lower doses than ISIS 2922.

EXAMPLE 11

ISIS 2922 can be used in combination with other antiviral drugs

ISIS 2922 was evaluated for antiviral activity in combination with compounds currently used for treatment of human CMV or HIV infection. ISIS 2922 anti-human CMV activity was additive with that of ganciclovir (DHPG) or foscarnet, and was not adversely affected by AZT or ddC.

EXAMPLE 12

Additional oligonucleotides targeted to immediate early genes and DNA polymerase A series of 21 phosphorothioate oligonucleotides were examined for anti-CMV activity. These oligonucleotides are shown in Table 4, with ISIS-2922 and a negative control oligonucleotide (ISIS 3383) shown for comparison.

TABLE 4

Anti-CMV activity of phosphorothioate oligonucleotides

| ISIS # | TARGET | SEQUENCE | IC$_{50}$ (µM) | SEQ ID NO: |
|---|---|---|---|---|
| 4733 | IE 5'UTR | TATGGAGGTCAAAACAGCGTG | 0.6 | 44 |
| 4734 | IE 5'UTR | TGGATCGGTCCCGGTGTCTTC | 0.3 | 45 |
| 4741 | IE 5'UTR | ACCGTTCCCGGCCGCGGAGGC | 1.3 | 46 |
| 4748 | IE 5'UTR | GGGGAATCCGCGTTCCAATGC | 0.2 | 47 |
| 4797 | Pol CR1 | CACCCGCGACCGCACCGCCGG | 1.3 | 48 |
| 4840 | Pol AUG | CAGATACGGGTTGAAAAACAT | 0.2 | 49 |
| 4845 | Pol 5'UTR | TGGTGTAAGGCGGAGCCGCCG | 1.4 | 50 |
| 4846 | Pol 5'UTR | TGGTGTAAGGCGGGGCCGCCG | 0.5 | 51 |
| 4847 | Pol 5'UTR | CAGACGGGCCAGGGCCAGAAG | 0.9 | 52 |
| 4848 | Pol 5'UTR | CAGACGGGCCGGGGCCAGAAG | 0.7 | 53 |
| 4849 | Pol 5'UTR | TCCTGCGTGCCAGTCTGTCCG | 0.55 | 54 |
| 4850 | Pol 5'UTR | GTAGCCGTTTTTGCGATGTCG | 0.3 | 55 |
| 4854 | Pol 5'UTR | CCTCCTGGTTCAGACGTTCTC | 0.55 | 56 |
| 4855 | Pol 5'UTR | CAGTTTAACCCCGTATATCAC | 0.18 | 57 |
| 4856 | Pol 5'UTR | CAGCTTACGAAGCAAAATCAC | 0.7 | 58 |
| 4859 | Pol AUG | CATAGCGGACCGTGAGAGGCT | 0.8 | 59 |
| 4860 | Pol AUG | CATAGCGGACCGTGGGAGGCT | 0.6 | 60 |
| 4861 | Pol AUG | CATAGCGGACCGTGAGGGGCT | 0.18 | 61 |
| 4866 | Pol AUG | CATAGCGGACCGTGGGGGGCT | 0.14 | 62 |
| 4867 | Pol CR2 | AAACCCACGGCGGGGCTGTGT | 0.45 | 63 |
| 4868 | Pol CR3 | CGCGCGATGGCCCCGGCCTGC | 1.4 | 64 |
| 2922 | IE2 | GCGTTTGCTCTTCTTCTTGCG | 0.2 | 22 |
| 3383 | negative control | | 3.0 | |

Oligonucleotides which inhibit CMV at one-third the dosage (or below) at which the negative control shows activity in this experiment (IC50=1 µM or less in this table) are preferred.

EXAMPLE 13

Chemical modifications of the ISIS 2922 and ISIS 3246 oligonucleotide sequences

Chimeric oligonucleotides were made in which the nucleotides in the center of the oligonucleotide are 2'-deoxynucleotides, but the flanking regions consist of 2'-O-methylated nucleotides. These chimeric oligonucleotides had phosphorothioate backbones and the same nucleotide sequence as ISIS 2922 (SEQ ID NO: 22). The chimeric oligonucleotides were active against CMV in the ELISA assay described in Example 5. ISIS 4325, which had 11 2'-deoxynucleotides flanked on either side by five 2'-O-methyl nucleotides, had an IC$_{50}$ of 0.5 µM. ISIS 4326, which had 7 deoxynucleotides flanked on either side by 7 2'-O-methyl nucleotides, had an IC$_{50}$ of 0.8 µM.

Several oligonucleotides sharing the same sequence (SEQ ID NO: 22) and having a 2'-O-methyl modification on every nucleotide were tested in this assay, and demonstrated IC$_{50}$s of 2.0 µM (phosphorothioate backbone) and >5.0 µM (phosphodiester backbone). These values were 80% and >200%, respectively, of the IC$_{50}$ obtained with a negative control oligonucleotide.

Chemical modifications of ISIS 3246 (SEQ ID NO: 24) were also tested for activity against CMV. These oligonucleotides are targeted to the 5'cap region of the human CMV IE mRNA. The oligonucleotides, modifications, and IC$_{50}$s for these oligonucleotides, along with parallel controls, are shown in Table 5:

TABLE 5

2' modifications of oligonucleotides targeted to the 5' cap of human CMV IE mRNA (SEQ ID NO: 24)

| ISIS # | CHEMICAL MODIFICATION | IC$_{50}$ (µM) |
| --- | --- | --- |
| 3246 | P=S | 0.7 |
| 3300 | P=S, uniform 2'-O—methyl | 0.3 |
| 3904 | neg. control: P=S, uniform 2'-O—methyl | 3.0 |
| 3300 | P=S, uniform 2'-O—methyl | 0.2 |
| 4155 | P=S, uniform 2'-O—propyl | 0.2 |
| 2922 | pos. control: P=S | 0.2 |
| 4952 | uniform 2'-fluoro | >4.0 |
| 4979 | P=S, uniform 2'-fluoro | 0.6 |
| 922 | pos. control: P=S | 0.3 |

Oligonucleotides having IC50s of 1 µM or below in Table 5 are preferred.

---

What is claimed is

1. An oligonucleotide comprising SEQ ID NO: 22.

* * * * *